United States Patent [19]

Eberwine et al.

[11] Patent Number: 5,922,553
[45] Date of Patent: Jul. 13, 1999

[54] METHOD OF DETECTING PROTEIN BY IMMUNO RNA

[75] Inventors: James Eberwine; Lori Rodgers, both of Philadelphia, Pa.

[73] Assignee: Trustees of the University of Pennsylvania, Philadelphia, Pa.

[21] Appl. No.: 08/972,225

[22] Filed: Nov. 17, 1997

Related U.S. Application Data

[60] Provisional application No. 60/033,338, Nov. 21, 1996.

[51] Int. Cl.$^6$ .................................................. G01N 33/543
[52] U.S. Cl. ............................ 435/7.92; 435/7.94; 435/6; 436/518
[58] Field of Search .................................. 435/7.92, 7.94, 435/6; 436/518, 811

[56] References Cited

U.S. PATENT DOCUMENTS

| 5,492,812 | 2/1996 | Vooheis ...................................... 435/7.1 |
| 5,514,545 | 5/1996 | Eberwine ...................................... 435/6 |
| 5,665,539 | 9/1997 | Sano et al. ...................................... 435/6 |

OTHER PUBLICATIONS

Bondareff et al., Absence of Abnormal Hyperphosphorylation of Tau in Intracellular Tangles in Alzheimer's Disease, Journal of Neuropathology and Experimental Neurology 54(5):657–683, 1995.

Sarkar and Sommer, "Acess to a Messenger RNA Sequence or Its Protein Product IS Not Limited by Tissue or Species Specificity", 1989 Science, 244:331–334.

Suzuki et al., "Double Determinant Immuno–Polymerase Chain Reaction: A SSensitive Method for Detecting Circulating Antigens in Human Sera", 1995 Jpn. J. Cancer Res., 86:885–889.

Boehringer Mannheim Catalog, Boehringer Mannheim Corporation, Indianapolis IN 1991, p. 164.

Carpenter et al., "A Transcriptionally Amplified DNA Probe Assay with Ligatable Probes and Immunochemical Detection", 1993 Clin Chem., 39(9) :1934–1938.

Eberwine et al., Analysis of gene expression in single live neurons, 1992 Proc. Natl. Acad. Sci., 89:3010–3014.

Joerger et al., "Analyte Detection with DNA–Labeled Antibodies and Polymerase Chain Reaction", 1995 Clin. Chem., 41(9) :1371–1377.

Krieg and Melton, "Efficient in vitro synthesis of biologically active RNA and RNA hybridization probes from plasmids containing a bacteriophage SP6 promoter", 1984 Nucl. Acid Res., 12:7035–7070.

Mackler and Eberwine, "Diversity of Glutamate Receptor Subunit mRNA Expression within Live Hippocamal CA1 Neurons", 1993 Mol. Pharm., 44:308–315.

Milligan et al., Oligoribonucleotide synthesis using T7 RNA polymerase and synthetic DNA templates, 1987 Nucl. Acid. Res., 15:8783–8798.

Ruzicka et al., "Immuno–PCR with a Commerically Available Avidin System", 1993 Science, 260:698–699.

Sanna et al., "Rapid induction of tumor necrosis factor α in the cerebrospinal fluid after intracerebroventricular injection of lipopolysaccharide revealed by a sensitive capture immuno–PCR assay", 1995 Proc. Natl. Acad. Sci., 92:272–275.

Sano et al., "Immuno–PCR: Very Sensitve Antigen Detection by Means of Specific Antibody–DNA Conjugates", 1992 Science, 258:120–122.

Van Gelder et al., "Amplified RNA synthesized from limited quanitities of heterogenous cDNA", 1990 Proc. Natl. Acad. Sci., 87:1663–1667.

Zhou et al., "Universal immuno–PCR for ultra–sensitive target protein detection", 1993 Nucleic Acid Res., 21:6038–6039.

Kreig and Melton, "Functional messenger RNAs are produced by SP6 in vitro transcription of cloned cDNAs", 1874 Nucl. Acid. Res., 12:7057–7070.

Sarkar and Sommer, "Access to a Messenger RNA Sequence or Its Protein Product Is Not Limited by Tissue or Species Specificity", 1989 Science, 244:331–334.

Suzuki et al., "Double Determinant Immuno–Polymerase Chain Reaction: A Sensitive Method for Detecting Circulating Antigens in Human Sera", 1995 Jpn. J. Cancer Res., 86:885–889.

Primary Examiner—Donna C. Wortman
Attorney, Agent, or Firm—Law Offices of Jane Massey Licata

[57] ABSTRACT

A method for the detection of a selected protein is provided wherein mRNA levels are correlated with the presence of protein using the technique referred to herein as immuno-aRNA.

3 Claims, No Drawings

METHOD OF DETECTING PROTEIN BY IMMUNO RNA

This application claims the benefit of U.S. Provisional Application No. 60/033,338, filed on Nov. 21, 1996, now abandoned.

FIELD OF THE INVENTION

The present invention relates to a method of detecting selected proteins in a sample by a technique referred to herein as immuno aRNA. Amounts of a selected protein detected by this method can then be correlated to the presence of various diseases. Accordingly, this method is useful in diagnosis of diseases.

BACKGROUND OF THE INVENTION

An analysis of specific mRNA levels in a given cell provides insight into the function and differentiative state of that particular cell at any point in its life cycle. However, mRNA levels do not always provide an accurate portrayal of a cell's functional state. It is the translated products of these mRNAs, such as the receptors, ion channels, enzymes, and structural proteins of the cell, that determine its function.

Techniques currently used to detect proteins are based on various types of immunoassays, such as ELISA, immunohistochemistry and radioimmunoassay, which utilize antibodies specific for the protein of interest. These immunoassays, while useful, are limited by the sensitivity of the detection of the antibody. Standard labeling methods include fluorescence, radioisotopes, and enzymes such as peroxidase and phosphatase. In addition, secondary antibodies are oftentimes biotinylated to increase their sensitivity. Still, these techniques are often not capable of detecting small amounts of a particular antigen. Furthermore, these types of techniques are not feasible for detection of a specific protein from a particular cell.

Electrophysiological techniques can detect protein from a specific cell. However, applications are limited to the monitoring of ion channel functioning, as well as the functioning of other receptors or proteins which are coupled to channels. It is difficult to detect the small amounts of other proteins that do not directly couple to ion channels, which techniques such as expression profiling and immunohistochemistry indicate are present and potentially regulated within an individual cell.

Recently, Sano et al., 1992 *Science*, 258:120–122, described an antigen detection technique termed immuno-polymerase chain reaction (immuno-PCR). This procedure provides an extremely sensitive method to detect proteins. In immuno-PCR, a linker molecule with bi-specific binding affinity for DNA and antibody is used to attach a marker DNA molecule specifically to an antigen-antibody complex, thus resulting in the formation of a specific antigen-antibody-DNA conjugate. The attached marker DNA can be amplified by PCR with the appropriate primers. The presence of specific size PCR products demonstrates that marker DNA molecules are attached specifically to antigen-antibody complexes thereby indicating the presence of antigen. As described by Sano et al. 1992, antigen is immobilized on the surface of microtiter plates and then detected by immuno-PCR. Using this technique, an approximately $10^5$ increase in sensitivity over an alkaline phosphatase conjugated ELISA was obtained. Sensitivity advantages of immuno-PCR have subsequently been confirmed in assays for mouse anti-lipoprotein IgG (Ruzicka et al., 1993 *Science*, 260:698–699); a human proto-oncogene protein (Zhou et al., 1993 *Nucleic Acid Res.*, 21:6038–6039); and tumor necrosis factor alpha (Sanna et al., 1995 *Proc. Natl. Acad. Sci.*, 92:272–275).

More recent reports have described advancements in immuno-PCR technology. For example, Joerger et al., 1995 *Clin. Chem.*, 41 (9):1371–1377) demonstrate that double-stranded DNA labels can be directly attached to antibodies thus allowing conjugate reagents to be prepared before the assay. Suzuki et al., 1995 *Jpn. J. Cancer Res.*, 86:885–889, describe a method called double determinant immuno polymerase chain reaction (double-determinant immuno-PCR) which utilizes two monoclonal antibodies, in which the antigens are sandwiched, and a specific DNA molecule is used as a marker. Instead of the antigen itself, the first monoclonal antibody to bind the circulating antibody is immobilized, the biotinylated second monoclonal antibody is bound to the antigen and free streptavidin is used to attach a biotinylated DNA to the second monoclonal antibody. The biotinylated DNA complexed with antigen-antibody-streptavidin is amplified by PCR, and the products analyzed by Southern blot analysis. While this technique has provided advantages over traditional methods of protein detection, such as an increase in sensitivity, there still exist several notable limitations. For example, the use of the polymerase chain reaction is not quantitative. While PCR can be used to "amplify" a marker sequence to detect rarely occurring proteins, this amplification is not quantitative for >10-fold differences in antigen concentration. Thus, there is no direct correlation between the amount of signal and the amount of protein present. The immuno-PCR method also has inherent limitations that make it difficult to detect the presence of antigen in a particular cell. This is particularly relevant when antigen expressed in a specific cell type, such as a neuron, is being assayed. Further, these detection techniques can only assay protein present in solution or tissue, which is often a mixture of cell types.

Accordingly, there exists a need for an easily adaptable, sensitive detection method that is semi-quantitative and that can provide an accurate protein profile for a specific cell.

SUMMARY OF THE INVENTION

An object of the present invention is to provide a method of detecting a selected protein by immuno aRNA. In this method, a first antibody targeted to the selected protein is immobilized to a solid support. The solid support with the immobilized first antibody is then contacted with the selected protein so that the selected protein binds to the immobilized antibody. The solid support is then contacted with a RNA-promoter driven cDNA sequence covalently coupled to a second antibody targeted to the selected protein so that the second antibody binds to selected protein bound to the immobilized first antibody on the solid support. The amount of selected protein in the cell is then determined by amplified RNA techniques which detect the bound promoter-driven cDNA sequence.

Amounts of selected protein can then be correlated to the presence of a disease. For example, in one embodiment, the method of the present invention was used to measure levels of tau protein in single cells such as neurons. Elevated levels of tau have been correlated to Alzheimer's disease. Accordingly, the method of the present invention will be useful in diagnosing diseases such as, but certainly not limited to, Alzheimer's disease.

DETAILED DESCRIPTION OF THE INVENTION

A technique known as amplified RNA (aRNA) synthesis has been developed and utilized in the past few years for a variety of purposes including in vitro RNA synthesis from plasmids containing the appropriate promoter site for use as probes (Melton et al., 1984 *Nucl. Acid Res.*, 12:7035–7056), for in vitro translation studies (Krieg and Melton, 1984 *Nucl.*

*Acid Res.*, 12:7057–7070), for producing synthetic oligonucleotides (Milligan et al., 1987 *Nucl. Acid Res.*, 15:8783–8798), and for detection of low abundance messages (Sarkar and Sinner, 1989 *Science*, 244:331–333; van Gelder et al., 1990 *Proc. Natl. Acad. Sci.*, 87:1663–1667; Carpenter et al., 1993 *Clin Chem.*, 39(9):1934–1938; Eberwine et al., 1992 *Proc. Natl Acad. Sci.*, 89:30-10–30-14; and Muckler and Eberwine, 1993 *Mol. Pharm.*, 44:308–315).

The technique of aRNA synthesis has been utilized by those of skill in the art perhaps most effectively for the detection of rare messages. In general, the first step in this method involves synthesizing an oligo(dT) primer that is extended at the 5' end with an RNA polymerase promoter such as the T7 or SP6 promoter. This oligonucleotide can be used to prime poly (A+) mRNA populations for cDNA synthesis. After the first strand cDNA is synthesized, the second strand cDNA is made, followed by RNA nuclease treatment to degrade the RNA and treatment with T4 DNA polymerase to generate a blunt-ended molecule. This double-stranded cDNA can then be used for amplification by utilizing the incorporated RNA polymerase promoter to direct the synthesis of RNA. The aRNA synthesized using this type of technique is quantitatively representative of the original message present in the population (van Gelder et al., 1990 *Proc. Natl. Acad. Sci.*, 87:1663–1667).

This method was further refined to assay the expression profile of a particular mRNA at the single cell level. Eberwine et al., 1992 *Proc. Natl Acad. Sci.*, 89:3010–3014. Using a variation of this technique, the mRNA from a defined single cell was characterized by microinjecting primer, nucleotides and reverse transcriptase using a patch pipette into acutely dissociated cells from a defined region of the rat brain. Patch clamp recording pipettes are ordinarily used to monitor and record changes in currents in response to depolarization of the cell (for ion channel functioning). A primary advantage of using this procedure is that the components that direct cDNA synthesis are brought into immediate contact with the mRNA in a contained environment (i.e., the cell and the patch pipette). This serves to increase the efficiency of conversion of mRNA to cDNA. Two rounds of amplification are sufficient for >$10^6$ fold amplification of the starting material which is adequate for analysis of the expression profile of rat hippocampus cells. In addition, by using the aRNA technique in conjunction with the patch pipette, several previously unidentified mRNAs from the hippocampal cells were detected. Most of these mRNAs are likely to be very low copy number messages not generally detectable due to dilution of individual mRNAs when isolated from tissue. Detection of these rare messages using this technique demonstrates the sensitivity of the aRNA procedure.

A modified aRNA technique has now been developed for use in the identification of proteins. The method of the present invention is especially useful in identification of proteins at the single cell level. This new method, termed immuno-aRNA, can accurately correlate the connection between coordinated mRNA level changes and the presence of protein. In this method a first antibody targeted to a first epitope of a protein of interest, i.e., the selected protein, is immobilized to a solid support by incubation at 4° C. Unattached first antibody is removed from the solid support by washing with buffer. This solid support containing the immobilized first antibody is then contacted with the selected protein so that the selected protein binds to the immobilized first antibody. The solid support is then contacted with a second antibody which recognizes a second epitope of the selected protein of interest and which is covalently coupled to a RNA promoter-driven cDNA sequence so that the second antibody binds to bound selected protein on the solid support. The promoter-driven cDNA sequence coupled to the second antibody is then used in an aRNA amplification procedure to detect the presence of the bound selected protein. aRNA synthesis is a technique known to those of skill in the art.

A variety of RNA promoters and RNA polymerases known to those of skill in the art can be utilized with this method. aRNA detection of conjugated antibody is more sensitive than standard fluorescence or peroxidase detection methods. Increased specificity is produced because two antibodies recognizing distinct regions of the protein must interact with the protein to detect a signal.

Antibody generation and selection for epitope specificity are techniques well known to those of skill in the art. Purified double stranded cDNA is attached to the selected antibody using glutaraldehyde and ethanolamine for extended periods of incubation. The antibody-DNA complex can be stored at 4° C. for subsequent use.

A variety of solid supports well known by those skilled in the art can be used in this method. Examples include, but are not limited to, siliconized patch pipettes, microtiter plates and beads. However, in a preferred embodiment, the solid support comprises a patch pipette. In this embodiment, the first antibody coated pipette tip is used to aspirate a sample containing the selected protein; in one embodiment, from an individual cell, in another embodiment, from serum, or in an additional embodiment, from solution. After a brief incubation, the pipette tip is washed to remove any non-specifically bound protein and the DNA-second antibody complex is aspirated into the tip. In this embodiment, aRNA can then be transcribed in the patch pipette using, for example, T7 RNA polymerase, three unlabeled ribonucleotides, one $^{32}$P labeled ribonucleotide and RNAsin. After incubation, a portion of the reaction is electrophoresed through an RNA denaturing gel. The gel is fixed, dried and placed on film for X-ray development. The presence and quantity of labeled RNA transcript is indicative of the amount of selected protein present.

The immuno aRNA technique of the present invention permits the detection of small amounts of protein-antibody complex by incorporating the sensitivity and accuracy of aRNA amplification. In one embodiment, this method provides increased sensitivity over standard protein detection methodologies by covalently coupling a T7 promoter driven cDNA sequence to the second antibody so that the nucleotide sequence can be amplified using T7 RNA polymerase. Double stranded cDNA is synthesized for use as a template for T7 RNA polymerase transcription. T7 RNA polymerase requires its promoter site to be double stranded. In order to generate this substrate, total spleen RNA is isolated for use as the starting material. Oligo-dT-T7 primer is added and allowed to anneal to the poly(A+) RNA present in the total RNA. First strand synthesis proceeds with the addition of AMV-reverse transcriptase and dNTPs. The first strand of cDNA is isolated and purified and used to synthesize the second strand of cDNA with the addition of T4 DNA polymerase, Klenow fragment, T7 oligo(dT), and dNTPs. The resulting double stranded CDNA is isolated and purified.

Experimental controls for the method of the present invention include one positive control, three negative controls, and three controls for specificity. The positive control consists of cross-linked antibody and DNA. The presence of signal demonstrates that the cDNA synthesis is successful and the aRNA amplification step can proceed. The negative controls are used to test for non-specific binding of the antibody-DNA complex and/or for non-specific aRNA amplification. They include; a solid phase, preferably a patch pipette, in which the antigen was not added, a solid phase, preferably a patch pipette, in which BSA is added in place of antigen, and a solid phase, preferably a patch pipetter, in which the antibody-DNA complex is not added (non-specific amplification). Controls used to ensure the specificity of antigen detection in a single cell include: harvesting of cells with a solid phase, preferably a patch pipette, coated with BSA only; cell contents harvested using solid phases, preferably patch pipettes which are not protein coated; and harvesting of cell media alone (pipette with antibody).

The method of the present invention which provides for the detection of a particular protein in a selected cell is especially useful in early diagnosis of diseases relating to expression of a particular protein in a specific cell type. For example, the method of the present invention was used to detect tau protein present in a single hippocampal neuron. Methods of detecting the presence of tau protein in the blood are disclosed in the art as being useful in confirming clinical diagnosis of Alzheimer's disease. See, e.g., U.S. Pat. No. 5,492,812. Accordingly, the present invention which provides a means for detecting tau protein levels much earlier in single cells can be used to diagnose Alzheimer's disease at a much earlier stage of the disease. As will be obvious to those of skill in the art upon this disclosure, however, the method of the present invention can be used in diagnosing any disease which has been correlated to expression of a particular protein.

The following examples are provided for illustrative purposes only and are not intended to limit the invention.

EXAMPLES

Example 1

Preparation of Double-Stranded DNA Tag Utilizing the Oligonucleotide-dt-T7 Primer Double stranded cDNA was generated from the single stranded oligonucleotide because the T7 RNA polymerase requires the promoter site to be double stranded. Total spleen RNA (approximately 9 $\mu$g) was denatured for three minutes at 95° C. and cooled on ice for five minutes to keep the strands separated. Approximately 20 $\mu$g of oligo-dt-T7 oligonucleotide (5'-AAAACGACGGCCAGTGAATTGT-AATACGACTCACTATGGGCGCTTTTTTTTTTTTTT-TTTTTTTTT-3' (SEQ ID NO: 1)) was added to 100 $\mu$g of total RNA in the presence of 1× reverse transcriptase buffer (50 mM Tris base, pH 7.5; 120 mM KCl; 10 mM MgCl$_2$), 10 mM dithiothreitol, 4 dNTPs at 250 $\mu$M each, and 0.5 $\mu$l of RNAsin.

The mixture was placed at 37° C. for 10 minutes to allow the poly A+ RNA present in the total RNA to anneal to the oligonucleotide. AMV-reverse transcriptase (1.2 U/$\mu$l) was added and the reaction was incubated at 37° C. for 60 minutes to synthesize the first strand of cDNA. Following the incubation, the single stranded cDNA was phenol extracted and precipitated. The second strand of cDNA was synthesized using 0.05 U/$\mu$l of T4 DNA polymerase and 0.05 U/$\mu$l of Klenow fragment in the presence of 1× KFI buffer (20 mM Tris-base, pH 7.5; 10 mM MgCl$_2$; 5 mM NaCl; 5 mM DTT), 4 dNTPs at 250 $\mu$M each, and 5 ng/$\mu$l of T7 oligo d(T)24. Following an incubation at 14° C. for 16 hours, the double stranded cDNA was phenol extracted and precipitated.

Example 2

Attachment of Double Stranded cDNA Tag to Tau-1 Antibody

Tau-1 antibody (100 $\mu$g) was added to purified double stranded cDNA tag (10 $\mu$g). An equal volume of 0.1% glutaraldehyde (EM grade) was added in 10 $\mu$l aliquots with mixing following each addition. The antibody and cDNA were incubated at room temperature for three hours with occasional mixing. A $\frac{1}{20}$ volume of 1M ethanolamine pH 7 was added and the mixture was incubated for an additional two hours at room temperature. The antibody-DNA complex was stored at 4° C. until subsequent use.

Example 3

Preparation of Patch Pipettes

Capillary tubes (0.8–1.10×100 mm, Kimax products) were siliconized and pulled into patch pipettes. Non-purified tau-46 (1 $\mu$l) was pulled into the tip of the pipettes and the pipettes were placed in 4° C. overnight to allow the antibody to attach to the inside of the tip. Pipettes were rinsed three times with phosphate buffered saline (PBS) by gently pulling the PBS into the tip and stored at 4° C. until needed.

Example 4

Attachment of Recombinant Tau Protein and Tau-1/DNA Complex

Recombinant tau protein (1 $\mu$g) was drawn into the pipette tip and incubated at 4° C. for 30 minutes. The pipette was rinsed three times with PBS and 2 $\mu$l of the antibody/DNA complex (approximately 40 ng of DNA) was drawn into the pipette tip. The pipette was incubated at 4° C. for 30 minutes. Following the second incubation, the pipette was rinsed three times with PBS and the tip of the pipette was crushed into the bottom of an eppendorf tube.

Example 5 aRNA Amplification

Tag amplification was performed by aRNA synthesis using T7 RNA polymerase (100 U/$\mu$l) in the presence of 1× RNA amplification buffer (40 mM Tris-base, pH 7.5, 7 mM MgCl$_2$); 10 mM MgCl$_2$; 2 mM spermidine); 5 mM dithiothreitol; 250 $\mu$M of ATP, UTP, GTP; 12.5 $\mu$M CTP; 30 uCi of $\alpha$-$^{32}$P-CTP; and 0.5 $\mu$l RNAsin. The reaction mixture was incubated at 37° C. for four hours. $\frac{1}{5}$ of the reaction was loaded into an RNA denaturing gel (1% agarose/formaldehyde) and electrophoresed at 50 Volts for two hours. The gel was immersed in 10% trichloroacetic acid for one hour with a solution change after 30 minutes. The gel was placed on PARAFILM (a flexible, semi-transparent, water resistant barrier for sealing of containers and tubes) and overlaid with 3 M Whatman paper and paper toweling to dry it. The gel was dried overnight and placed on X-ray film for a three hour and a 24 hour exposure. Amplification products were present in the positive control and in samples, but not in the negative controls.

Example 6

Immuno-aRNA as Applied to Detection of Tau Protein in a Single Cell

The procedure as described in the preceding five examples was used to harvest the protein from a single cell. The cells used were rat hippocampal neurons in primary culture (3 weeks) They were patched onto the cell by methods known to those of skill in the art, with the antibody coated patch pipette and the cellular contents aspirated into the pipette. The remainder of the procedure is as described in the preceding examples. Various controls were performed to ensure the specificity of the technique including 1) harvesting of cells with patch pipettes coated with just BSA, 2) cell contents harvested using patch pipettes which were not protein coated, 3) harvesting of cell media alone (pipette with Ab). These controls show the specificity of the reaction. A broad range of aRNA observed in individual cells shows that these cells contain tau protein.

antibody targeted to the selected protein so that the second antibody binds to the bound selected protein on the solid support; and

---

---

What is claimed is:

1. A method for quantifying levels of a selected protein by immuno-aRNA comprising:

a) immobilizing a first antibody targeted to a selected protein to a solid support;

b) contacting the solid support with the selected protein so that the selected protein binds to the immobilized first antibody;

c) contacting the solid support with a RNA promoter-driven cDNA sequence covalently coupled to a second d) quantifying levels of the promoter-driven cDNA sequence covalently coupled to the bound second antibody by amplified RNA techniques as an indication of the amount of selected protein present.

2. The method of claim 1 wherein a T7 promoter driven cDNA sequence is covalently coupled to the second antibody.

3. The method of claim 1 wherein the selected protein is tau.

* * * * *

SEQUENCE LISTING (1) GENERAL INFORMATION:

(iii) NUMBER OF SEQUENCES:  1

(2) INFORMATION FOR SEQ ID NO: 1:

(i) SEQUENCE CHARACTERISTICS:
      (A) LENGTH:  67
      (B) TYPE:  Nucleic Acid
      (C) STRANDEDNESS:  Single
      (D) TOPOLOGY:  Linear (iv) ANTI-SENSE:  No (xi) SEQUENCE DESCRIPTION:  SEQ ID NO: 1:

```
AAAACGACGG CCAGTGAATT GTAATACGAC TCACTATGGG CGCTTTTTTT           50

TTTTTTTTTT TTTTTTT                                               67
```